United States Patent
Liddell et al.

[11] 4,314,764
[45] Feb. 9, 1982

[54] CHEMICAL ANALYSIS SAMPLE CONTROL

[75] Inventors: Peter R. Liddell, North Bayswater; Antony S. Pearl, desceased, late of Griffith, Australia; by Edmund Calvert, administrator, Canberra, Australia

[73] Assignee: Varian Tectron Party Ltd., Victoria, Australia

[21] Appl. No.: 952,176

[22] Filed: Oct. 17, 1978

[30] Foreign Application Priority Data

Oct. 18, 1977 [AU] Australia .............................. PD2098

[51] Int. Cl.³ ............................................ G01N 21/72
[52] U.S. Cl. .................................... 356/315; 356/417
[58] Field of Search ......................... 356/315, 316, 417

[56] References Cited

PUBLICATIONS

"Atomic Absorption"; Bausch & Lomb; Rochester, N.Y.; Nov. 1967; The Sum of the Parts Section.
Spectro chimica Acta., vol. 29B, pp. 19–31; Jan. 1974; Pergamon Press 1974; Printed in Northern Ireland.
Analytical Chemistry, vol. 48 #11, Sep. 1976; Montaser et al., pp. 1490–1499.

Primary Examiner—Vincent P. McGraw
Attorney, Agent, or Firm—Stanley Z. Cole; Gerald M. Fisher

[57] ABSTRACT

A method of controlling spectroscopic analysis in which a sample in liquid concentrate form and containing an element of interest, is nebulized and carried into an analysis zone by pressurized support gas. The invention comprises regulating the flow rate of the support gas to control the density of atoms of the element present in the analysis zone so as to be within a measurable range. The flow of support gas controls sample uptake at the nebulizer, and that uptake is reduced by dividing the gas flow before the nebulizer so that one part bypasses the nebulizer but is nevertheless directed into the analysis zone so that the total gas flow to the analysis zone remains constant. In spectroscopic apparatus for carrying out that method, the gas flow rate through the nebulizer is automatically reduced when an overrange condition is detected, and a correction factor is applied to the apparatus read-out for each reduction in that flow rate so that the read-out at all flow rates is representative of the quantity of the element of interest in the sample.

22 Claims, 4 Drawing Figures

ABSORBANCE vs CONCENTRATION
ELEMENT: COPPER
WAVELENGTH: 324·7nm

CHEMICAL ANALYSIS SAMPLE CONTROL

This invention relates to chemical analysis of samples by spectroscopic techniques, and is especially although not exclusively concerned with flame spectrometry. The invention is applicable to atomic absorption, fluorescence, and emission spectroscopy, but it will be convenient to hereinafter describe the invention in relation to atomic absorption flame spectroscopy.

The purpose of analysis by atomic absorption flame spectrometry is to determine the presence of an element of interest in a particular sample, and in carrying out the analysis a solution containing that sample is sprayed into the flame. Practical difficulties arise however, if the concentration of the element in the sample is outside a particular range. For most elements, the concentrations measurable by flame atomic absorption cover a range of about 1000. The lower limit is set by the minimum absorbance signal which can be observed above the baseline noise, and the upper limit is set by the curvature of the calibration (the change in absorbance for a given change in concentration becomes progressively smaller and more difficult to determine) and/or increased noise due to the high absorbance.

If the concentration of an element in a sample is above the upper limit of measurement, it has been the practice prior to this invention, to adopt one of the following procedures:

(a) change the wavelength of the monochromator of the instrument used in carrying out the analysis, to a less sensitive line;
(b) rotate the burner of the instrument;
(c) change to a less sensitive flame or burner;
(d) dilute the sample.

These techniques all require intervention of the operator to carry out time consuming instrument adjustment or sample treatment. Furthermore, they are not readily amenable to automation.

It is a primary object of the present invention to provide a method of conveniently extending the measurable concentration range, and which can be adapted to automatic operation if desired. A further object of the invention is to provide apparatus for carrying out that method.

The usual method of introducing the sample solution into the flame is by means of a nebulizer, which generally utilizes nitrous oxide or air under pressure to nebulize the sample and carry it into the flame. The present invention is based on the appreciation that the atom density in the flame is dependent on the rate of uptake of the sample to the flame, and that is in turn dependent upon the support gas flow. Consequently, if the gas flow is reduced, there will be a corresponding reduction in the atom density in the flame, which is a result comparable to diluting the sample. Thus, a particular concentration of an element in a sample which is too high to be measured in the normal manner, can be made to give an absorbance reading within the measurable range.

A method according to the invention is therefore characterized in that it involves adjustment of the support gas flow to extend the range of measurable concentrations of an element in a sample. Such adjustment is convenient to effect and can be controlled to give a predictable change in the atom density in the flame, so that accurate assessment of the analysis results is possible. Also, the flow adjustment is readily adaptable to automatic control if required.

According to one aspect of the invention there is provided a method of controlling spectroscopic analysis of a sample including the steps of, feeding a sample in liquid concentrate form to a nebulizer, said sample including an element of interest, feeding a support gas under pressure to the nebulizer to nebulize said sample and to carry the nebulized sample into an analysis zone, and controlling the flow of said support gas to said nebulizer to regulate the flow rate of said sample to said analysis zone and to thereby control the density of atoms of said element present in said analysis zone so as to be within a measurable range.

According to a further aspect of the invention there is provided apparatus for use in spectroscopic analysis of a sample, including, a nebulizer for atomizing a sample in liquid concentrate form; a gas feed line and a sample feed line, each of which is connected to said nebulizer; a gas supply line connectable to a gas source and to said gas feed line; an excess gas flow line connectable to said gas supply line; and flow control means operable in a first condition to direct gas flow from said gas supply line into said gas feed line to the exclusion of said excess gas flow line, and in a second condition to direct that gas flow into both said gas feed line and said excess gas flow line.

If the invention is applied to atomic absorption spectroscopy, it is convenient to use the level of radiant energy absorbed by the atoms of interest in the sample, as the controlling parameter for the purpose of determining when the sample flow rate should be changed. In the case of fluorescence and emission spectroscopy, the radiant energy emitted by the atoms can be used for the foregoing purpose.

The essential features of the invention, and further optional features, are described in detail in the following passages of the specification which refer to the accompanying drawings. The drawings however, are merely illustrative of how the invention might be put into effect, so that the specific form and arrangement of the features (whether they be essential or optional features) shown is not to be understood as limiting on the invention.

Figure 1:
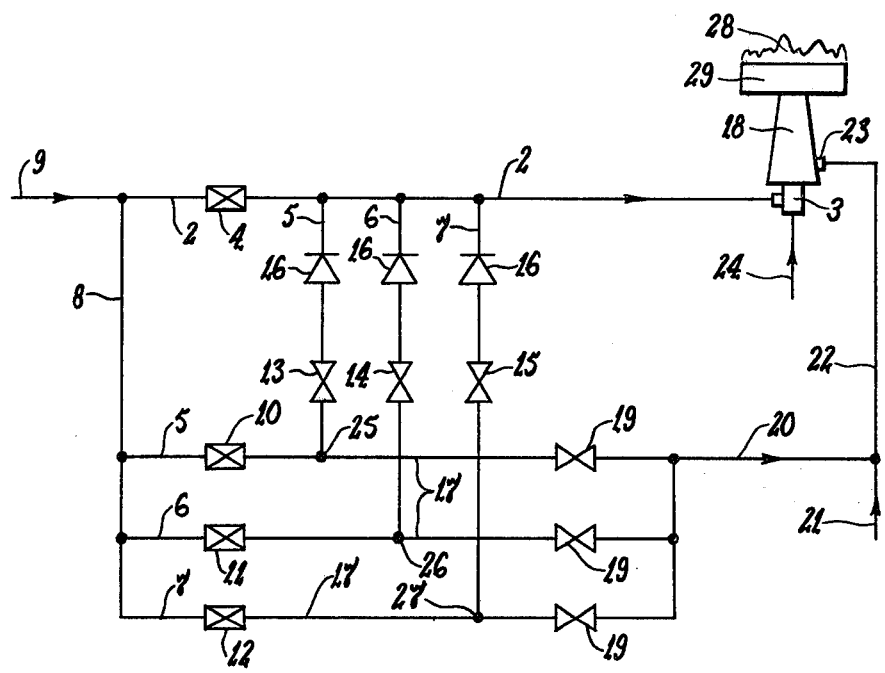
FIG. 1 is a schemmatic diagram of one possible embodiment of the invention as applied to flame spectroscopy.

In the particular embodiment of the invention shown by FIG. 1, the feed line 2 which conveys support gas to the nebulizer 3, is provided with a control valve 4, and each of a plurality of by-pass lines 5, 6 and 7 is connected to the gas feed line 2 on both the upstream and downstream sides of the control valve 4. As shown, each by-pass line 5, 6 and 7 may be connected to a common transfer line 8 which is connected to the feed line 2 at the upstream side of the control valve 4, and has independent connection with the feed line 2 on the downstream side of the control valve 4. A supply line 9 connects the feed line 2 with a suitable source of support gas, which is an oxidant.

Each by-pass line 5, 6 and 7 includes a control valve 10, 11 and 12 respectively, a flow restrictor 13, 14 and 15 respectively, and a non-return valve 16, arranged in that order when considered from the transfer line or inlet end. Each of the flow restrictors 13, 14 and 15 may be of any suitable form—e.g., a needle valve or fixed orifice—and each of the non-return valves 16 is arranged to prevent gas in the feed line 2 on the downstream side of the valve 4, flowing backwards through the respective by-pass line 5, 6 or 7.

Each of the flow restrictors 13, 14 and 15 is adapted to have a different capacity such that the maximum flow rate through each by-pass line 5, 6 and 7 is different. It is preferred that each by-pass flow restrictor 13, 14 and 15 is arranged so that the maximum flow is less than that available through the feed line 2. By way of example, in the arrangement shown, the three by-pass lines 5, 6 and 7 may be arranged to allow respective flow rates such as to provide attenuation of the atom density by nominal factors of 10, 100 and 1000.

An excess gas flow line 17 is connected to each by-pass line 5, 6 and 7 at a location between the respective by-pass control valve 10, 11 and 12 and flow restrictor 13, 14 and 15, and is preferably arranged to direct gas to the nebulizer spray chamber 18. As shown, each excess flow line 17 may include an appropriate flow restrictor 19 and may communicate with the spray chamber 18 through a common discharge line 20. In the arrangement shown, the discharge line 20 connects with a fuel gas line 21, so that the excess oxidant and the fuel gas (e.g. acetylene) are fed together through line 22 to an auxiliary inlet 23 of the spray chamber 18.

When the arrangement described is in normal use, the feed or main control valve 4 is open and each of the by-pass or secondary control valves 10, 11 and 12 are closed. Consequently, uptake of the sample entering the nebulizer 3 through line 24 is influenced by the gas flow rate directly through the feed line 2, and that is no different to conventional systems. If however, the concentration of the element in the sample falls outside the measurable range, the main control valve 4 is closed and a selected secondary control valve 10, 11, or 12, is opened. Gas flow is thereby transferred to the selected by-pass line 5, 6, or 7, and that flow is split at the respective excess flow junction 25, 26, or 27, so that one part proceeds to the nebulizer 3 by way of the feed line 2 and thereby influences sample uptake, and the other part proceeds directly to the spray chamber 18 and has no influence on sample uptake. A reduction in sample uptake naturally follows and the effect of that reduction on atom density in the flame can be determined because the flow rate through the operative by-pass line is known. A further consequence of the split flow system is that the total gas supply to the flame 28 generated by burner 29, is the same whether the flow is direct through the feed line 2 or through one of the by-pass lines 5, 6 and 7.

It will be apparent that the arrangement described can be adapted for automatic operation. For example, when the instrument response is such as to indicate that the concentration of the element in the sample is not within the measurable range, suitable means operates to close the main control valve 4 and open a secondary valve 10, 11, or 12. The selection of an appropriate by-pass 5, 6 or 7 may be achieved by stepping through the available by-passes 5, 6 and 7, working from the lowest flow reduction towards the highest, until the instrument response indicates that a satisfactory atom density in the flame has been obtained.

The instrument response necessary for the foregoing may be achieved through electronic circuitry substantially the same as that previously used in conventional spectrometry instruments to provide a visual indication that the concentration of the element in the sample under analysis is outside the measurable range. That response circuitry can be adapted to operate solenoids or other suitable valve actuators such that the desired automatic flow correction is obtained.

An instrument incorporating flow control apparatus as described can be calibrated in the usual manner for the normal working range of the instrument—i.e., one or more standards would be used. Additional standards of concentration compatible with that of each extended range as represented by a particular flow by-pass, would then be used to calibrate for each extended range. In using the calibrated instrument, unknown samples would be aspirated in the normal way. If the concentration of an element in a particular sample was above the normal range, the instrument would automatically switch to the appropriate extended range and the concentration would be read out directly. Such an arrangement would not require any operator intervention.

Figure 2:
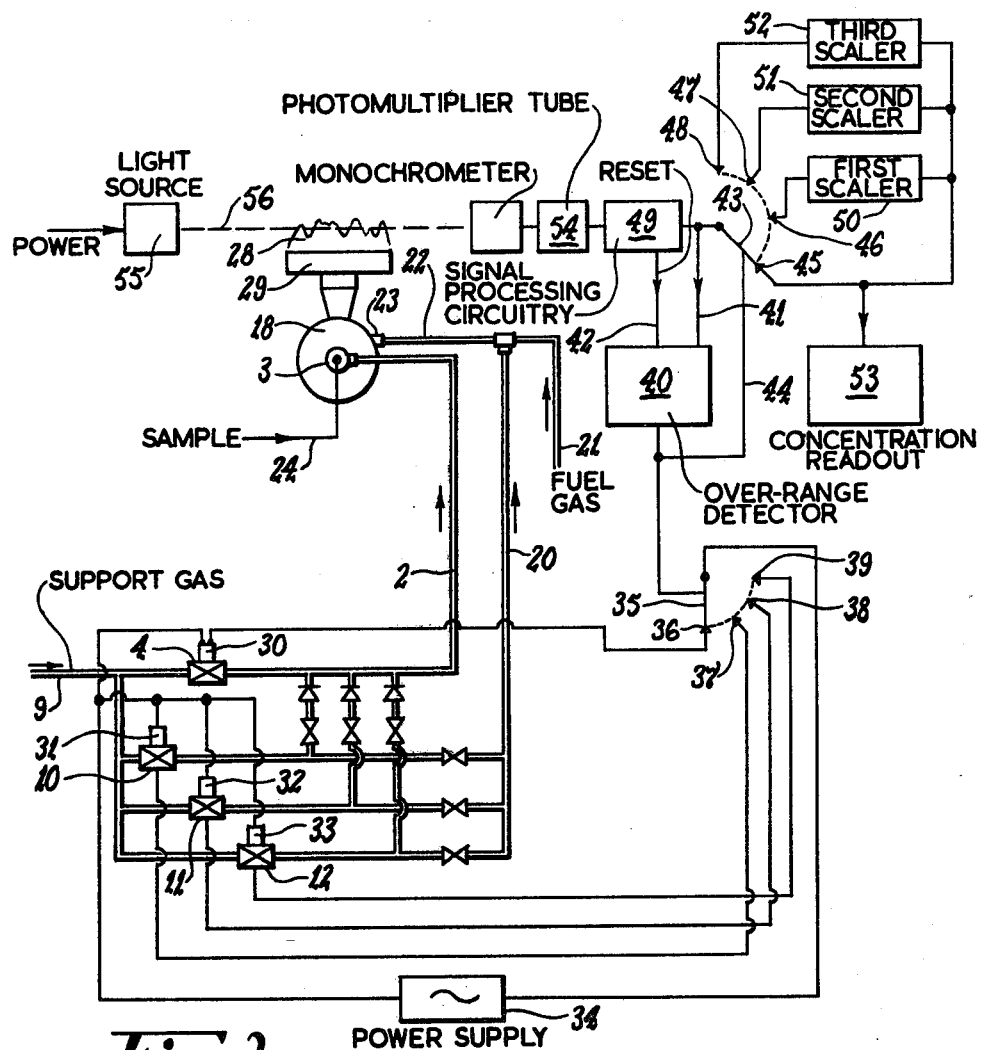
FIG. 2 is a schemmatic diagram similar to FIG. 1 and showing the embodiment of FIG. 1 connected to an atomic absorption spectrophotometer.

By way of further example, FIG. 2 provides a diagrammatic representation of a spectrophotometer incorporating apparatus of the kind described in relation to FIG. 1. In the particular construction shown, each of the valves 4, 10, 11 and 12 is actuated by a respective solenoid 30, 31, 32 and 33 arranged to be connected to a power source 34 through switch 35. In the condition shown in FIG. 2, switch 35 is closed on contact 36 so that solenoid 30 is energized and valve 4 is open, but movement of the switch 35 to close on any one of the other contacts 37, 38 or 39 will result in opening of valve 10, 11 or 12 respectively.

Movement of switch 35 is controlled through an over-range detector 40, which may include a comparator of any suitable form arranged to compare an in-coming signal—i.e., along path 41—with a pre-set level. Re-set path 42 permits passage of a signal to the detector 40 such that it can be re-set for each subsequent comparison operation.

The detector 40 also functions to apply a correction factor to the read-out function of the instrument each time the range concentration is changed. In that regard, the output of the detector 40 is connected to a further switch 43 through conductive path 34, and in the example shown the switch 43 can adopt any of four operative positions in which it closes on contact 45, 46, 47 or 48 respectively. FIG. 2 shows the switch 43 in the position corresponding to the normal range of sample concentration in which the main valve 4 is open and the secondary valves 10, 11 and 12 are closed.

In the event that detector 40 detects an over-range condition, it will generate a signal which causes a change in the operative position of both switches 35 and 43. Switch 35 will close on contact 37 and thereby cause valve 4 to close and valve 10 to open, and switch 43 will close on contact 46 so that the output of the signal processing circuitry 49 is directed through scaler 50 to the read-out unit 53. Scaler 50 is operative to modify the signal passing to the unit 53 so that it reflects the change in sample concentration brought about by opening valve 10, and for that purpose it may include an appropriate amplifier circuit. If an over-range condition is still detected by detector 40, the switches 35 and 43 will move onto contacts 38 and 47 respectively so that valve 11 is open and scaler 51 becomes operative to apply a correction factor compatible with the resulting change in sample concentration. Scaler 52 provides yet another correction factor for when valve 12 is open to achieve a still higher concentration range.

The signal processing circuitry 49 and the read-out unit 53 may be of conventional form. For example, the circuitry 49 may include a suitable amplifying circuit for converting the output signal of the photomultiplier tube 54 into logarithmic form, and the unit 53 may include a digital volt meter, analogue meter, or other appropriate read-out means.

As in conventional atomic absorption spectroscopy, the light source 55 directs a beam 56 through the nebulized sample in the flame 28, which constitutes the analysis zone of the instrument. The sample is thereby irradiated, and the radiant energy absorbed by the atoms of interest is detected by the photomultiplier tube 54 in a known manner to produce a signal characteristic of the level of that absorption. The subsequent processing of that signal through circuitry 49 and read-out unit 53, which could be referred to in combination as analogue means, results in a signal which is characteristic of the quantity of the element of interest in the sample, and again that is achieved in a known manner.

Figure 3:
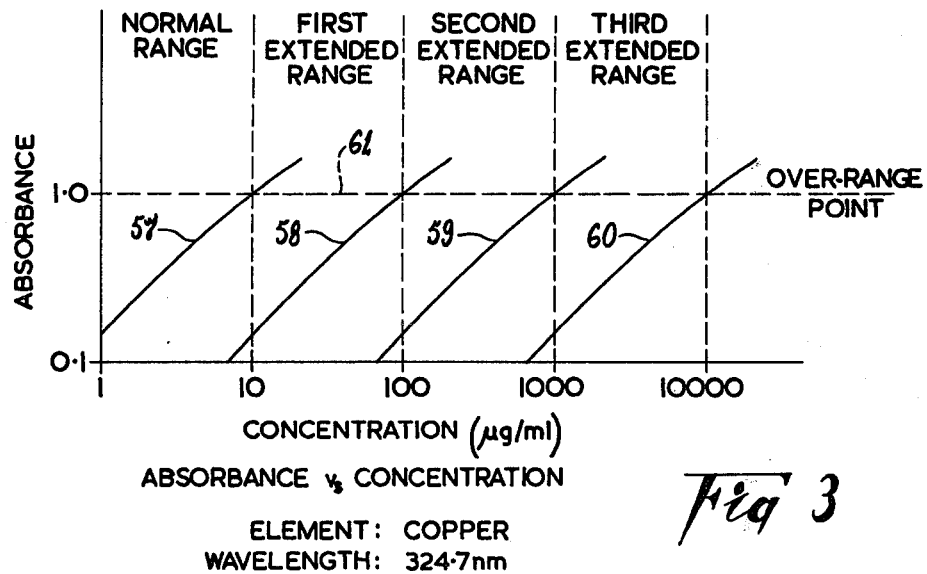
FIG. 3 is a graph showing the consequence of changing the sample flow rate in the construction according to FIG. 2.

FIG. 3 is a graph showing absorbance against sample concentration measured in micrograms per milliliter. In the particular example shown, the element of interest in the sample was copper and the relevant wavelength was 324.7 nanometers. Line 57 represents the level of absorbance over a concentration range of 1:10, which is termed the "normal range". At concentrations beyond 10 $\mu$g/ml, the absorbance line 57 exceeds what, in this example, is considered the over-range point which is represented by broken line 61. The instrument is then switched to the first by-pass position comparable to closing valve 4 and opening valve 10 of the FIG. 1 arrangement, and that results in the first extended range of concentration which embraces concentrations of 10 to 100 $\mu$g/ml. At concentrations beyond 100 $\mu$g/ml, the absorbance line 58 goes beyond the over-range point 61, so that switching to the second extended range is required and absorbance line 59 results. In a third extended range, absorbance line 60 is created. As previously explained, when an extended range is utilized, a suitable correction factor is applied to the absorbance read-out to compensate for change in sample concentration.

Figure 4:
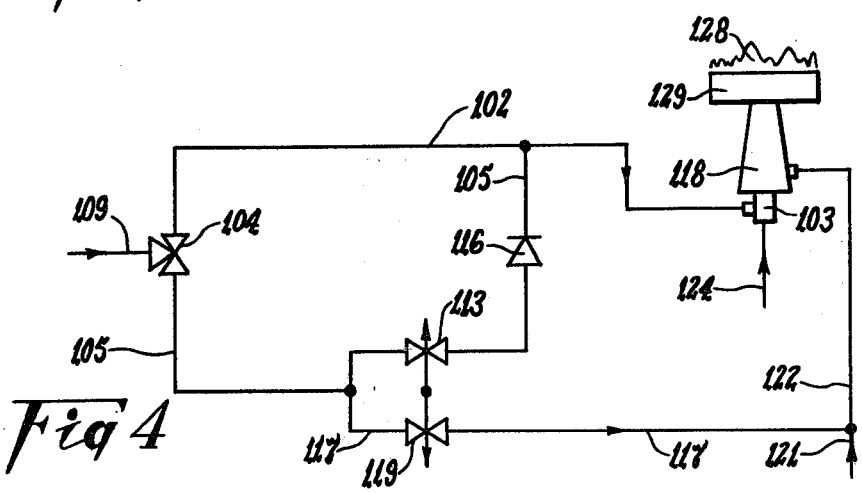
FIG. 4 is a view similar to FIG. 1 but showing an alternative embodiment of the invention.

FIG. 4 shows one form of an alternative to the arrangement described in relation to FIG. 1, in which the measurable concentration may be extended through a single variable attenuation factor rather than through three fixed factors (i.e., the by-pass flow restrictors 13, 14 and 15 of the FIG. 1 arrangement. Components of the FIG. 4 arrangement corresponding to components of the FIG. 1 arrangement, will be given like reference numerals but which are included in the series 100 to 199. In the example of FIG. 4, the feed control valve 4 of the FIG. 1 arrangement is substituted by a change-over valve 104 having a divided outlet flow facility. One outlet flow of that device is along the feed line 102 to the nebulizer 103, and the other is into the inlet of a single by-pass line 105 which has its outlet connected to the feed line 102 between the nebulizer 103 and the change-over valve 104. Either outlet can be selected according to requirements as discussed in relation to the previous arrangement—i.e., the by-pass outlet will be selected for concentrations outside the measurable range. If desired, two separate valves could be substituted for the single change-over valve 104. An excess flow line 117 extends from the upstream side of the by-pass flow restrictor 113 to the spray chamber 118 as in the previous arrangement.

The flow restrictor 113 has a variable restriction facility so as to replace the three by-pass restrictors (13, 14 and 15) of the FIG. 1 arrangement, and that may be achieved through a needle valve associated with the flow restrictor 113. As shown, a similar variable restriction facility is preferably provided in the flow restrictor 119 of the excess flow line 117. It is further preferred, again as shown, that the variable restriction devices 113 and 119, whatever their form, be interconnected so that one opens in automatic response to the other closing, and vice versa.

In normal operation of the FIG. 3 arrangement, the change-over valve 104 is adjusted to provide flow through the feed line 102 only. If the measurable concentration range needs to be extended, the change-over valve 104 is operated to divert flow to the by-pass line 105, and the variable restrictors 113 and 119 are preset to provide a particular rate of flow through the by-pass 105 and into the feed line 102. Excess flow is diverted through the variable restrictor 119 direct to the spray chamber 118 and has no influence on sample uptake, and the consequence is as described in the first arrangement. It will be appreciated that, because of the interconnection of the flow restrictors 113 and 119, the excess flow restrictor 119 opens as the by-pass flow restrictor 113 closes so that the total flow capacity remains unchanged. Actuation of the change-over valve 104, and possibly the variable restrictors 113 and 119, can be effected automatically as also previously described.

In the FIG. 1 arrangement, the three switchable steps enable the measurable concentration to be extended by a factor of up to 1000. In the alternative arrangement of FIG. 4, the variable restrictor 113 enables the attenuation factor to be preset at any desired value between 1 and 1000, or any other range as may be required. The FIG. 4 arrangement can be incorporated in a spectrophotometer in a manner similar to that shown by FIG. 2.

It will be apparent from the foregoing that the invention provides a method and apparatus which conveniently and effectively enables the range of concentrations measurable by flame atomic absorption, and other forms of spectroscopy, to be extended by a factor of 1000, or some other factor as may be desired. Appropriate calibration procedures and electronic processing enables the apparatus to operate automatically and to provide a direct read-out of the correct concentration. Such a result is not possible with previously known techniques.

Finally, it is to be understood that various alterations, modifications and/or additions may be introduced into the constructions and arrangements of parts previously described without departing from the spirit or ambit of the invention as defined by the appended claims.

Having now described our invention, what we claim as new and desire to secure by Letters Patent is:

1. A method of controlling dilution of sample concentration for spectroscopic analysis of a sample including the steps of, receiving light in a photodetector characteristic of said sample, feeding a sample in liquid concentrate form to a nebulizer, said sample including an element of interest, feeding a support gas under pressure to the nebulizer to nebulize said sample and to carry the nebulized sample into an analysis zone, and controlling the flow of said support gas to said nebulizer to regulate the rate of said sample to said analysis zone and to thereby control the density of atoms of said element present in said analysis zone so as to be within a measurable range, controlling said flow of support gas to said nebulizer in response to said photodetector response, said control providing division of said support gas before said nebulizer so that part of said support gas only influences the uptake of said sample at said nebulizer, and the remainder of said support gas flow is fed to said analysis zone through a pass by-passing said nebulizer.

2. A method according to claim 1, wherein the flow rate of the sample uptake part of said support gas flow is controlled by selecting any one of a plurality of nebulizer by-pass paths for said remainder of the support gas flow, each said path having a different flow rate potential.

3. A method according to claim 1, wherein the flow rate of the sample uptake part of said support gas flow is controlled by adjusting a variable restrictor in said nebulizer by-pass path to limit the flow rate through that path to a suitable level.

4. A method according to claim 1, wherein the support gas flow by-passing said nebulizer is increased to cause a further reduction in the support gas flow to said nebulizer, and the sum total of said two said flows remains substantially constant at all times.

5. A method according to claim 1, wherein a light beam is passed through said analysis zone to cause irradiation of atoms of said element present in said analysis zone, the level of radiant energy absorbed by said irradiated atoms is detected by said photodetector and processed by electronic means and converted by that means into a signal characteristic of the density of said atoms present in said analysis zone, a comparison means for issuing a command to said control means when said signal indicates that the density is above the linear measurable range, and a correction factor is applied to said electronic means when the support gas flow rate to said nebulizer is less than the maximum, to compensate for reduction in the density of said atoms in said analysis zone, and the value of said correction factor is varied according to the flow rate of said support gas to said nebulizer.

6. A method according to claim 4, wherein the level of radiant energy emitted by atoms of said element of interest present in said analysis zone, is detected by electronic means and converted by that means into a signal characteristic of the density of said atoms present in said analysis zone for controlling the increase of support gas flow, and a correction factor is applied to said electronic means when the support gas flow rate to said nebulizer is less than the maximum, to compensate for reduction in the density of said atoms in said analysis zone, and the value of said correction factor is varied according to the flow rate of said support gas to said nebulizer.

7. A method according to claim 6, wherein a light beam is passed through said analysis zone to cause irradiation of said atoms.

8. Apparatus for use in spectroscopic analysis of a sample, including a photodetector, a nebulizer for atomizing a sample in liquid concentrate form, a gas feed line and a sample feed line, each of which is connected to said nebulizer, a gas supply line connectable to a gas source and to said gas feed line, an excess gas flow line connectable to said gas supply line, and flow control means operable in a first condition to direct gas flow from said gas supply line into said gas feed line to the exclusion of said excess gas flow line, and in a second condition to direct that gas flow into both said gas feed line and said excess gas feed line, a spray chamber having a primary inlet and an auxiliary inlet, said spray chamber is connected to said nebulizer so as to receive said nebulized sample through said primary inlet, and said excess gas flow line is connected to said auxiliary inlet to introduce gas to said spray chamber, and means responsive to said photodetector output for measuring and determining if the sample concentration exceeds the linear measurable range and for commanding said flow control means to change from said first condition to said second condition.

9. Apparatus according to claim 8, wherein a by-pass line is connected between said gas supply line and said excess gas flow line and is also connected to said gas feed line; said control means includes valve means which is operative in said first condition to prevent passage of gas to said gas feed line by way of said by-pass line, and in said second condition to connect said gas supply and feed lines in gas flowing relationship by way of said by-pass line; and said control means further includes flow restrictor means located downstream of said valve means and which is operative, in said second condition, to cause a predetermined part of the total gas flow received from said gas supply line, to be diverted from said by-pass line through said excess gas flow line.

10. Apparatus according to claim 9, wherein said valve means includes a main control valve and a secondary control valve located in said gas feed line and said by-pass line respectively, said by-pass line is connected to said gas feed line at two locations which are upstream and downstream respectively of said main control valve, said excess gas flow line is connected to said by-pass line at a location downstream of said secondary control valve, said main and secondary control valves are open and closed respectively in said first condition and are closed and open respectively in said second condition, and said flow restrictor means is located downstream of said secondary control valve and is operative to cause a predetermined part of the total gas flow to enter said gas feed line through said by-pass line.

11. Apparatus according to claim 10, wherein said flow restrictor means includes a flow restrictor in each of said by-pass and excess gas flow lines, and both said flow restrictors are located downstream of the connection between said by-pass and excess gas flow lines.

12. Apparatus according to claim 10, wherein there is a plurality of said by-pass lines, each of which includes a respective said secondary control valve, and a separate said excess gas flow line is connected to each said by-pass line.

13. Apparatus according to claim 9, wherein said valve means comprises a change-over valve, both said gas feed and by-pass lines are connected to said gas supply line through said change-over valve, and said restrictor means is adjustable to vary the ratio of the gas flows, in said second condition, passing through said excess gas flow line and into said gas feed line through said by-pass line respectively.

14. Apparatus according to claim 13, wherein said restrictor means includes an adjustable flow restrictor in said by-pass line and a further adjustable flow restrictor in said excess gas flow line, and the two said flow restrictors are interconnected so that their permissible flow rates are increased and decreased respectively with adjustment, and so that any increase in the permissible flow rate of one corresponds to the decrease in the permissible flow rate of the other.

15. A spectrophotometer including, apparatus according to claim 8, an analysis zone which receives a nebulized sample from said nebulizer, means operative to cause irradiation of said nebulized sample within said analysis zone, electrical means responsive to said irradiation to provide a signal characteristic of the quantity of an element in said sample, and correction means operative to convert said flow control means from said first condition to said second condition when said irradiation exceeds a predetermined level, and being further operative to apply a correction factor to said electrical means to compensate for the resulting decrease in the density of said nebulized sample in said analysis zone.

16. A spectrophotometer according to claim 15, including a burner which is operative to generate a flame in said analysis zone.

17. A spectrophotometer according to claim 16, wherein said flame comprises said irradiation means.

18. A spectrophotometer according to claim 15, wherein said irradiation means comprises a light source arranged to direct a beam of light through said analysis zone.

19. A spectrophotometer according to claim 18, wherein said electrical means includes detector means operative to generate an electrical signal characteristic of the level of radiant energy absorbed by said irradiated sample, and analogue means responsive to said electrical signal to provide a measure of the quantity of said element in the sample, said correction means is responsive to the level of said radiant energy absorbed and being operative to apply said correction factor to said analogue means.

20. A spectrophotometer according to claim 18, wherein said electrical means includes detector means operative to generate an electrical signal characteristic of the level of radiant energy emitted by said irradiated sample, and analogue means responsive to said electrical signal to provide a measure of the quantity of said element in the sample, said correction means is responsive to the level of said radiant energy emitted and being operative to apply said correction factor to said analogue means.

21. A spectrophotometer according to claim 15, wherein said flow control means is operative, in said second condition, to permit selection of any one of a plurality of ratios of the flow rates through said by-pass line and said excess gas flow line respectively, and said correction means is operative to apply a correction factor according to the particular ratio selected.

22. Atomic absorption spectrometer apparatus comprising:

a source lamp, a photodetector, a burner means mounted between said source lamp and said photodetector for providing a cloud of atoms into a beam of radiation directed from said source lamp towards said photodetector;

a carrier gas supply line;

nebulizer means having a first and second input and an output;

a gas feed line connected to flow gas from said carrier gas supply line to said nebulizer, said gas feed line being said nebulizer means first input;

a sample feed line connected to said nebulizer for providing sample liquid to said nebulizer, said sample feed line being said second input to said nebulizer;

said burner means including a chamber for receiving said nebulizer means output, said chamber also connected to an auxiliary input line, said auxiliary line for introducing flame supporting gases;

means for controllably dividing, in operation, flow gases in said carrier gas supply line between said gas feed line and an excess gas flow line, said excess gas flow line being connected to said auxiliary inlet line for assuring that the gas flow to said chamber is inversely proportional to the flow in said gas feed line whereby the total carrier gas flow to said burner is maintained at a predetermined rate said means for controllably dividing flow gases in said carrier gas supply line being responsive to said photodetector output signal.

* * * * *